(12) United States Patent
Alander et al.

(10) Patent No.: US 11,306,272 B2
(45) Date of Patent: Apr. 19, 2022

(54) ODOURLESS SHEA BASED ESTERS

(71) Applicant: AAK AB (PUBL), Malmö (SE)

(72) Inventors: Jari Alander, Danderyd (SE); Staffan Norberg, Karlshamn (SE)

(73) Assignee: AAK AB (PUBL), Malmö (SE)

( * ) Notice: Subject to any disclaimer, the term of this patent is extended or adjusted under 35 U.S.C. 154(b) by 0 days.

(21) Appl. No.: 16/093,167

(22) PCT Filed: Apr. 12, 2017

(86) PCT No.: PCT/SE2017/050369
§ 371 (c)(1),
(2) Date: Oct. 12, 2018

(87) PCT Pub. No.: WO2017/180051
PCT Pub. Date: Oct. 19, 2017

(65) Prior Publication Data
US 2019/0127661 A1    May 2, 2019

(30) Foreign Application Priority Data
Apr. 13, 2016  (SE) .................................. 1650500-0

(51) Int. Cl.
| | | |
|---|---|---|
| C11B 3/14 | (2006.01) | |
| A61K 8/37 | (2006.01) | |
| B01D 3/38 | (2006.01) | |
| A23D 9/013 | (2006.01) | |
| A61Q 19/00 | (2006.01) | |
| C11B 3/00 | (2006.01) | |
| A23D 9/007 | (2006.01) | |
| C11C 1/10 | (2006.01) | |
| C11C 1/08 | (2006.01) | |
| C11C 3/00 | (2006.01) | |
| C11C 1/00 | (2006.01) | |
| A61Q 5/00 | (2006.01) | |
| A61Q 17/04 | (2006.01) | |
| A23D 7/005 | (2006.01) | |

(52) U.S. Cl.
CPC ............... *C11B 3/14* (2013.01); *A23D 9/007* (2013.01); *A23D 9/013* (2013.01); *A61K 8/37* (2013.01); *A61Q 5/00* (2013.01); *A61Q 17/04* (2013.01); *A61Q 19/00* (2013.01); *A61Q 19/001* (2013.01); *A61Q 19/007* (2013.01); *B01D 3/38* (2013.01); *C11B 3/003* (2013.01); *C11C 1/002* (2013.01); *C11C 1/08* (2013.01); *C11C 1/10* (2013.01); *C11C 3/003* (2013.01); *A23D 7/005* (2013.01); *A61K 2800/10* (2013.01); *A61K 2800/5922* (2013.01)

(58) Field of Classification Search
CPC .. A61K 2300/00; A61K 8/922; A61K 36/185; A61K 36/28; A61K 36/286; A61K 36/31; A61K 36/48; A61K 36/54; A61K 36/55; A61K 36/63; A61K 36/889; A61K 36/899; A61K 8/375; A61K 2800/10; A61K 2800/5922; A61K 31/047; A61K 31/22; A61K 31/575; A61K 8/37; A61K 8/86; A61K 8/63; A61K 8/925; A61K 2800/48; A61K 8/31; A61K 8/361; A61K 8/72; A61K 8/8111; A61K 31/355; A61K 38/1825; A61K 38/1841; A61K 38/1866; A61K 38/1891; A61K 38/40; A61K 31/4985; A61K 9/0053; A61K 9/4858; A61K 9/16; A61K 9/4825; A61K 9/485; A61K 9/4891; A61K 9/2013; A61K 9/2054; A61K 47/38; A61K 9/0019; A61K 9/0024; A61K 9/10; A61K 9/1617; A61K 9/1635; A61K 9/1641; A61K 9/1652; A61K 9/2027; A61K 9/2031; A61K 9/4866; A61K 45/06; A61K 9/20; A61K 9/2009; A61K 9/284; A61K 9/48; A61Q 19/00; A61Q 17/04; A61Q 19/001; A61Q 19/007; A61Q 1/06; A61Q 5/00; A61Q 5/02; A61Q 17/00; A23L 33/115; A23L 33/15; A23L 33/16; A23L 33/17; C07D 471/16
See application file for complete search history.

(56) References Cited

U.S. PATENT DOCUMENTS

| | | | |
|---|---|---|---|
| 2008/0057552 A1* | 3/2008 | Lee ........................... | C11C 3/10 435/134 |
| 2009/0148433 A1* | 6/2009 | Naidu .................. | A61K 31/355 424/94.61 |

FOREIGN PATENT DOCUMENTS

| | | |
|---|---|---|
| CN | 103445996 A | 12/2013 |
| EP | 1 001 007 A1 | 5/2000 |

(Continued)

OTHER PUBLICATIONS

Akhisa et al., "Antiinflammatory and chemopreventive effects of triterpene cinnamates and acetates from shea fat", J Oleo Sci, 59(6): 273-280, (2010). (Year: 2010).*

(Continued)

*Primary Examiner* — Audrea B Coniglio
(74) *Attorney, Agent, or Firm* — Finnegan, Henderson, Farabow, Garrett & Dunner, LLP

(57) ABSTRACT

There are provided odorless shea based esters as an ingredient composition comprising: a) 81-97 wt % of at least one short chain alcohol alkyl ester, at least partially from a natural source, b) 3-19 wt % of triterpene esters where at least one is a cinnamic triterpene ester, and c) 1100 ppm or less of at least one short chain alcohol cinnamic ester. There is further provided a method of manufacturing the composition comprising a deodorization step. An advantage is that an odourless or an almost odourless composition can be provided.

23 Claims, No Drawings

(56) References Cited

FOREIGN PATENT DOCUMENTS

| EP | 1001007 A1 * | 5/2000 | ............... A23L 9/22 |
| JP | 1-275700 | 11/1989 | |
| NL | 1001007 A1 * | 5/2000 | ............... C11C 1/04 |
| WO | WO 03/099240 A1 | 12/2003 | |
| WO | WO 2015/047187 A1 | 4/2015 | |

OTHER PUBLICATIONS

Vicenzo et al., "Regional Variation in shea butter lipid and triterpene composition in four African countries," J Agric Food Chem, 53(19), 7473-7479, (2005). (Year: 2005).*

Asihisa, T. et al. ("Anti-Inflammatory and Chemopreventive Effects of Triterpene Cinnamates and Acetates from Shea Fat", J. Oleo. Sci, May 2010, vol. 59, No. 6, pp. 273-280) (Year: 2010).*

Akihisa et al., "Anti-inflammatory and chemopreventive effects of triterpene cinnamates and acetates from shea fat," J Oleo Sci, 59(6):273-280, (2010).

Čmolík et al., "Physical refining of edible oils," Eur J Lipid Sci Technol, 102:472-486, (2000).

International Search Report for International Application No. PCT/SE2017/050369, dated Jun. 16, 2017.

Vincenzo et al., "Regional variation in shea butter lipid and triterpene composition in four African countries," J Agric Food Chem, 53(19):7473-7479, (2005).

Written Opinion of the International Searching Authority for International Application No. PCT/SE2017/050369, dated Jun. 16, 2017.

* cited by examiner

ODOURLESS SHEA BASED ESTERS

This application is a national stage filing under 35 U.S.C. § 371 of International Application No. PCT/SE2017/050369, filed on Apr. 12, 2017, which claims the benefit of the filing date of Swedish Patent Application No. 1650500-0, filed on Apr. 13, 2016, each of which is incorporated herein by reference.

TECHNICAL FIELD

The present invention relates generally to a cosmetic alkyl ester composition without a fruity (cinnamic) scent, made from vegetable oils containing cinnamic esters and other potential "fruit esters", this without reducing the unsaponifiable matter in the vegetable oil while the undesired volatile fragrant esters are removed.

PRIOR ART

A typical cosmetic and personal care formulation contains 10 to 50 ingredients. Each ingredient contributes with its individual value to the formulation. The formulation is created to give specific values to the consumer. However, the scent or fragrance of the formulation is the one feature which is universal throughout all formulations and a key decision factor for the consumer.

Many consumers, especially in Asia prefer non-fragranced products while others, typically in the Western world prefer well fragranced formulations. The brands are using perfume to differentiate from competition, to enhance an emotion, attract specific consumer categories and so on.

Regardless of the consumer preferences, the ingredients which are not considered as a perfume need to be odorless to become a versatile building block within the cosmetic and personal care industry. If not, they can only be used in small quantities or special cases by certain brands, as they will either hinder an odor free formulation or interfere with the formulators' task to deliver a specific scent sensation in a formulation.

Shea butter is one of the most popular vegetable oils used in the field of cosmetics and personal care today. The liquid fraction of shea butter, shea butter oil or shea olein, stands out in the market of vegetable oils within the cosmetic market for several reasons and is well perceived by the consumer. As a basic delivery it combines a liquid appearance with good oxidation stability. It gives good moisturisation properties but the differentiation factor beyond all is the high content of unsaponifiable matter, especially triterpene alcohol esters. The typical level of triterpene esters in a shea butter oil is between 6-10 wt. % by weight.

The main triterpene alcohols in shea butter are lupeol, alpha-amyrin, beta-amyrin, butyrospermol and parkeol (Peers, J. Sci. Food Agric. 28(11), 1000-1009, (1977).) The triterpene alcohols are esterified with mainly three types of acids: long chain fatty acids, acetic acid and cinnamic acid. Around half of the triterpenes are esterified with cinnamic acid, e.g. around 4 wt. % of the shea olein contains triterpene cinnamates.

The triterpene esters are shown to hold anti-ageing and anti-inflammatory properties, often sought for within cosmetic applications (Akihisa et al J Oleo Sci, 59(6), 273-280 (2010).).

Vegetable oils including shea butter oil have received a large popularity the last years for their ability to bring emolliency to the skin. However in Asia and the growing men's care business a common trend for less greasy formulations has grown. Botanical ingredients which can deliver non-oily skin feel with excellent emolliency are sought for.

Shea butter oil ethyl esters are one answer to this and can be produced by transesterification of shea butter oil and ethanol from a botanical or synthetic source. As the main feature, defining shea from other vegetable oils, is the amount of triterpene esters known for their anti-ageing and anti-inflammatory properties, retaining the triterpene esters in such shea butter oil ethyl ester is a key requirement. Other similar raw materials containing relevant amounts of triterpene esters or sterol esters include rice bran oil, corn fiber oil, avocado oil and similar.

Ethyl cinnamate is the ester of cinnamic acid and ethanol. It is present in the essential oil of cinnamon. Pure ethyl cinnamate has a "fruity and balsamic odor, reminiscent of cinnamon with an amber note".

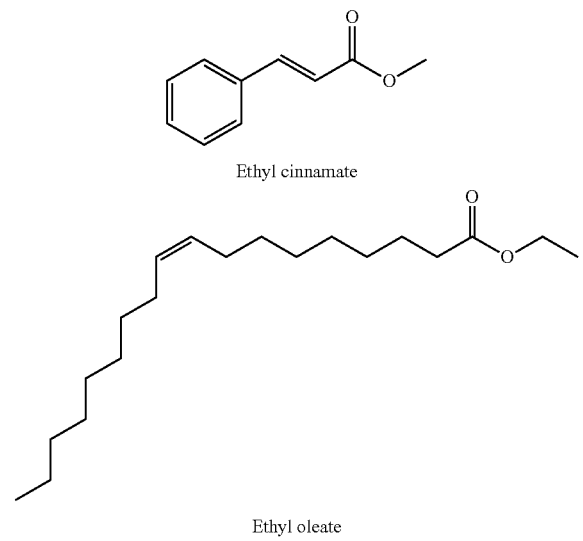

Ethyl cinnamate

Ethyl oleate

The boiling point for ethyl oleate is similar to ethyl stearate and ethyl linoleate, as it is the number of carbons that determine the boiling point and other physical properties. Ethyl palmitate has consequently a slightly lower boiling point.

The boiling point for the triterpene esters are much higher than for both ethyl oleate as well as ethyl cinnamate. They have high solubility in oil and non-polar organic solvents.

However, as the shea butter oil triterpene esters contains around 4 wt. % of cinnamates, also ethyl cinnamate is potentially created during the transesterification process.

Ethyl cinnamate in turn gives a fruity scent which hinders its usage in most cosmetic applications, both in applications requiring non-fragranced formulations and in fragranced formulations where it will interfere with the perfume added, inhibiting the possibility to create a distinct and differentiated scent of the final formulation. Thus the invention aims at solving this problem and provide odorless ingredients.

The published application WO 2015/047187 discloses a method of separating alkyl esters from triterpene esters. The intention of that invention is to produce a concentrate of triterpene esters, not to produce an alkyl ester retaining a natural level of minor components (unsaponifiables). The publication is discussing the removal of ethyl cinnamates along with simultaneous removal of the long chain fatty acid ethyl esters such as ethyl oleate, ethyl palmitate, ethyl stearate, and ethyl linoleate. The document is silent about removal of ethyl cinnamates only.

EP1001007 describes a process of enriching a sterol fraction in a shea glyceride oil from its original level of 7.5% sterol content to a concentrate between 12-20%. The concentrate is made with a chemical modification followed by an evaporation step above 200 degrees C. The result of the method is a change in composition with reduced triglyceride levels and increased levels of diglycerides and sterols. The concentrate is then further blended with other sterol/oil blends and used in food applications.

There is thus a need for removal of volatile esters of cinnamic acid and its' analogues, isomers and derivatives due to their scent without removing the unsaponifiables and long chain fatty acid ethyl esters. The present invention addresses such needs and interests.

SUMMARY

The inventors have found a window where the unsaponifiables, mainly triterpene esters, and long chain fatty acid ethyl esters remain in the distillation residue while the ethyl cinnamate is removed with the distillate.

In a first aspect there is provided an ingredient composition comprising:
a) 81-97 wt. % of at least one short chain alcohol alkyl ester, at least partially from a natural source,
b) 3-19 wt. % of triterpene esters where at least one is a cinnamic triterpene ester, and
c) 1100 ppm or less of at least one short chain alcohol cinnamic ester.

In a second aspect there is provided a method to reduce the amount of ethyl cinnamate to 1100 ppm or less in a composition of ethyl esters of shea butter with a content of triterpene esters (unsaponifiables) of 5-9 wt. %, said method comprising deodorization.

In a third aspect there is provided the use of an ingredient composition as described above for at least one selected from the group consisting of
as an ingredient for a personal care applications,
as an ingredient for a cosmetic application,
as an ingredient in a skin care formulation,
as an ingredient in a hair care formulation,
as an ingredient in a lip care formulation,
as an ingredient in a color cosmetic formulation,
as an ingredient in a sun care application,
as an ingredient in at least one selected from a lotion, ointment, and cream,
as a constituent in in soft-shelled capsule
as an ingredient in a food application, and
as a release agent in food application.

One advantage of the invention is that ethyl cinnamate and other volatile esters of cinnamic acid and its' analogues, isomers and derivatives, can be removed so that an odorless or almost odorless composition can be obtained.

DETAILED DESCRIPTION OF INVENTION

Before the invention is disclosed and described in detail, it is to be understood that this invention is not limited to particular compounds, configurations, method steps, substrates, and materials disclosed herein as such compounds, configurations, method steps, substrates, and materials may vary somewhat. It is also to be understood that the terminology employed herein is used for the purpose of describing particular embodiments only and is not intended to be limiting since the scope of the present invention is limited only by the appended claims and equivalents thereof.

It must be noted that, as used in this specification and the appended claims, the singular forms "a", "an" and "the" include plural referents unless the context clearly dictates otherwise.

As used throughout the description and the claims the term "natural source" in connection with a short chain alcohol alkyl ester denotes that it comes from a natural source, i.e. its chemical synthesis has occurred in nature such as in a plant. Natural source thus means that the ester is from a living organism such as a plant.

If nothing else is defined, any terms and scientific terminology used herein are intended to have the meanings commonly understood by those of skill in the art to which this invention pertains.

Under normal atmosphere the boiling points found at the internet for some of the molecules is described in the table. Lupeol acetate and lupeol cinnamate represent the components which are meant to remain in the distillation residue. Ethyl oleate and ethyl stearate represent the main long chain fatty acid ethyl esters which shall remain in the distillation residue, while ethyl cinnamate is the molecule needed to be removed.

| | Boiling point* (° C.) |
|---|---|
| Lupeol acetate | 503 |
| Lupeol cinnamate | 488 |
| Ethyl cinnamate | 271 |
| Ethyl oleate | 210 |
| Ethyl stearate | 214 |

*Boiling points at 760 mmHg.

Thus it can be seen that the boiling point of ethyl cinnamate which should be removed is between the boiling points of the other compounds that should remain in the composition. Thus a simple distillation cannot solve the problem.

Similar considerations may be made for other volatile esters of cinnamic acid and its' analogues, isomers and derivatives that may be present in the vegetable oil used as starting raw material. For example, rice bran oil is known for contain triterpene ferulates, i.e. esters of triterpene alcohols with ferulic acid ((E)-3-(4-hydroxy-3-methoxy-phenyl)prop-2-enoic acid). Cinnamic acid also exists in a trans-isomer (most abundant in shea butter) as well as a cis-isomer. Cinnamic acid analogues such as phenyl-propanoic acid or cyclohexyl propanoic acid are also conceivable if the raw material is subjected to hydrogenation. All these possible modifications are included by reference in the scope of the invention.

The present invention uses shea butter as raw material, but is not limited to shea butter and therefore rice bran and other vegetable oils containing cinnamic acid isomers, derivatives and their esters can also be utilized as raw material.

Ethyl cinnamate is molecule which gives a characteristic fruity scent, even at a rather low level. The concentration required for the scent to become noticeable to human beings is called the odor threshold value. Below this value human being will not recognize any scent of the molecule.

Deciding the exact level is rather difficult as the individual ability to sense a certain scent varies largely, Another factor is the matrix in which the molecule, here ethyl cinnamate, exists. In wine, which is largely polar (comprising mainly water and ethanol), a level as low as 1 ppm of ethyl cinnamate is reported as the odor threshold level.

The shea butter oil ethyl ester is a non-polar matrix and thus the solubility of ethyl cinnamate is higher than in wine, thus a higher odor threshold value can be expected.

The inventors have estimated the threshold value of ethyl cinnamate in a shea butter oil ethyl ester to be between 700 ppm to 1100 ppm. As indicated in the experimental section the threshold value can be considered to be 700 ppm. However in an alternative embodiment the odor threshold value is 400 ppm.

The invention shows examples on how to remove volatile alkyl cinnamates in alkyl ethyl esters such as methyl-long chain fatty acids, ethyl-long chain fatty acids and isopropyl-long chain fatty acids. Short chain alcohol alkyl esters are esters made by reacting methanol, ethanol or propanol. Examples of such short chain alcohol alkyl esters are ethyl alkyl esters, methyl alkyl ester, propyl alkyl ester or isopropyl ester.

The purpose for a distillation and/or deodorization is to by pressure and temperature separate two or more fractions. At a certain temperature and pressure, some molecules will remain (distillation residue) while other starts boiling and are removed in the so called distillate. Normally the boiling points and the partial vapor pressures of each ingredient determine which one to go and which to stay.

The conditions according to the invention during the deodorization will specifically remove the undesired ethyl cinnamate but will not remove desired compounds such as long chain alkyl ethylates and triterpene esters. At least it will not remove desired compounds to an extent so that it becomes a problem in the process.

In a first aspect there is provided an ingredient composition comprising:
a) 81-97 wt. % of at least one short chain alcohol alkyl ester, at least partially from a natural source,
b) 3-19 wt. % of triterpene esters where at least one is a cinnamic triterpene ester, and
c) 1100 ppm or less of at least one short chain alcohol cinnamic ester.

In one embodiment the at least one short chain alkyl esters are esters made by reacting methanol, ethanol or propanol. Thus, further embodiments are wherein the at least one short chain alkyl esters is ethyl alkyl ester, methyl alkyl ester, propyl alkyl ester or isopropyl alkyl ester.

In one embodiment the at least one short chain alcohol cinnamic acid esters is methyl-, ethyl-, propyl- or isopropyl cinnamate.

In one embodiment the at least one short chain alcohol cinnamic ester is ethyl cinnamate.

In one embodiment the composition comprises 800 ppm or less of the at least one short chain alcohol cinnamic ester.

In one embodiment the composition comprises 700 ppm or less of the at least one short chain alcohol cinnamic ester. The level of 700 ppm can be taken as the odor threshold as indicated in the experimental section.

In one embodiment the composition comprises 600 ppm or less of the at least one short chain alcohol cinnamic ester.

In one embodiment the composition comprises 400 ppm or less of the at least one short chain alcohol cinnamic ester.

In one embodiment the composition comprises 200 ppm or less of the at least one short chain alcohol cinnamic ester.

In one embodiment the composition comprises 100 ppm or less of the at least one short chain alcohol cinnamic ester.

In one embodiment the composition comprises 9-15% triterpene esters.

In a second aspect there is provided a method to reduce the amount of ethyl cinnamate to 1100 ppm or below in a composition of ethyl esters of shea butter with a content of triterpene esters (unsaponifiables) of 5-9 wt. %, said method comprising deodorization.

In one alternative embodiment the composition of ethyl esters of shea butter comprises 4-10 wt. % of triterpene esters (unsaponifiables). In most cases the interval of 5-9 wt. % of triterpene esters (unsaponifiables) corresponds to the natural content of triterpene esters (unsaponifiables) in shea butter. It is an advantage that the natural content of unsaponifiables can be kept as it is during the process.

In one embodiment the amount of ethyl cinnamate in both the first and second aspect is 800 ppm or less. In another embodiment the amount of ethyl cinnamate in both the first and second aspect is 700 ppm or less. In another embodiment the amount of ethyl cinnamate in both the first and second aspect is 600 ppm or less. In yet another embodiment the amount of ethyl cinnamate in both the first and second aspect is 400 ppm or less. In still another embodiment the amount of ethyl cinnamate in both the first and second aspect is 200 ppm or less.

In one embodiment at least 95 wt. % of the ingoing material to the deodorization remains in the composition with no chemical modifications after the deodorization. The ingoing material is the weight of the composition comprising the ester and which is subjected to deodorization. The ingoing material is thus the total weight of the material subjected to deodorization. The major part, i.e. at least 95 wt % of the material does not take part in any chemical reactions during the deodorization so that it is not chemically modified during the deodorization. In one embodiment at least 98 wt. % of the ingoing material to the deodorization remains in the composition with no chemical modifications after the deodorization. In one embodiment at least 99 wt. % of the ingoing material to the deodorization remains in the composition with no chemical modifications after the deodorization.

In one embodiment the amount of ethyl cinnamate is reduced to 700 ppm or below.

In one embodiment the content in the composition of any one of ethyl oleate, ethyl stearate, ethyl palmitate, and ethyl linoleate are not decreased with more than 2 wt % respectively during the deodorization.

In one embodiment the content of ethyl oleate is above 50 wt % and wherein the content of ethyl oleate is not reduced below 50 wt. % during deodorization.

In one embodiment the produced ethyl esters of shea butter are essentially odorless. In one embodiment the odorless means that the ethyl esters of shea butter comprise 400 ppm or less of any short chain alcohol cinnamic ester.

In one embodiment the temperature is in the interval 100-140° C. during the deodorization.

In one embodiment the pressure is in the interval 1-5 mbar during the deodorization.

In one embodiment the steam flow is in the interval 10-50 g/h during the deodorization.

In one embodiment at least one bleaching earth is added. Examples of bleaching earths include but are not limited to clay soil such as acid clay, activated earth and Fuller's earth. Fuller's earth is a mineral substance characterized by the property of absorbing basic colours and removing them from oils.

In a third aspect there is provided the use of an ingredient composition as described above for at least one selected from the group consisting of as an ingredient for a personal care applications,
as an ingredient for a cosmetic application,
as an ingredient in a skin care formulation,
as an ingredient in a hair care formulation,
as an ingredient in a lip care formulation,
as an ingredient in a color cosmetic formulation,
as an ingredient in a sun care application,
as an ingredient n at least one selected from a lotion, ointment, and cream,
as a constituent in in soft-shelled capsules,
as an ingredient in a food application, and
as a release agent in food application.

The amount of the ingredient varies in different applications. In a soft gel the amount is close to 100 wt % or even 100 wt %. In cosmetic applications the amount of the ingredient is often below 1 wt. %. Thus the amount of the ingredient according to the invention ranges from 0.3 wt. % to 100 wt. % depending on the application. The skilled person within the area of triterpene esters would know how much to use in different applications and can appreciate the low or non-existing odor of the ingredient according to the invention.

Raw materials that can be used for the present invention include the following, but are not limited to those described here. The below examples of raw materials serves as a guide for suitable raw materials to use when practicing the invention.

Different shea butters:

Shea Butter

Shea butter is most often obtained from the kernels of the species *Vitellaria paradoxa* from West Africa.

The suitable raw material is defined by an iodine value in the interval 60-70. It contains 5-9 wt. % of unsaponifiables of which 2-5 wt. % are in form of triterpene esters and the remaining part in form of karitene (high molecular weight hydrocarbon) and sterols and sterol esters at low concentrations. The remaining 91-95 wt. % of the composition are glycerides in forms of mono-, di- or triglycerides.

The exact fatty acid composition for shea butter varies as it is a natural raw material and grows in different parts of Africa.

A reaction with ethanol and shea butter with sodium ethylate as a catalyst would typically result in a composition between the following ranges:

|   | Min | Max |   |
|---|---|---|---|
| Ethyl oleate | 37 | 47 | wt. % |
| Ethyl stearate | 35 | 45 | wt. % |
| Ethyl palmitate | 2 | 6 | wt. % |
| Ethyl linoleate | 5 | 10 | wt. % |
| Unsaponifiable matter | 5 | 9 | wt. % |

Karitene may be removed by treating the oil with a polar solvent. This may reduce the iodine value to be just below 60.

One example of removal of karitene is according to the following. Refined shea butter is melted at 60° C. and then cooled 40° C. 1 kg of warm shea butter is blended with 4 liters of acetone at 40° C. The blend is cooled to 10° C. so that the karitene precipitates without oil precipitation. The blend is filtered to separate the karitene from the oil in acetone solution. The acetone from the dekaritenised shea butter is removed by vaporization at low pressure (100 mbar) and 60° C. The dekaritenised and de-solventized shea butter is used as raw material for further processing and modification.

Shea Butter Oil

Shea butter oil is obtained from shea butter by fractionation in a solvent such as hexane or acetone. The fractionation methods and the other types of solvents that may be used, are well known by those skilled in the art.

The shea butter may be of native type or of dekaritenised shea butter. (In the experimental section below, only dekaritenised shea butter is used.)

The raw material is defined by an iodine value in the interval 70-85. It contains 5-12 wt. % of unsaponifiables of which 5-11 wt. % are in form of triterpene esters and the remaining part in form of karitene and/or other typical constituents of the unsaponifiable fraction. The remaining 88-95 wt. % of the composition are glycerides in forms of mono-, di- or triglycerides.

The exact fatty acid composition for shea butter oil varies as it is a natural raw material and grows in different parts of Africa.

A reaction with ethanol and shea butter with sodium ethylate as a catalyst would typically result in a composition between the following ranges:

|   | Min | Max |   |
|---|---|---|---|
| Ethyl oleate | 45 | 60 | wt. % |
| Ethyl stearate | 23 | 30 | wt. % |
| Ethyl palmitate | 2 | 8 | wt. % |
| Ethyl linoleate | 5 | 10 | wt. % |
| Unsaponifiable matter | 5 | 12 | wt. % |

Shea Butter Stearine

Shea butter stearine is obtained from shea butter by fractionation in a solvent such as hexane or acetone. Other types of solvents may be used.

The raw material is defined by an iodine value in the interval 30-40. It contains 1-3 wt. % of unsaponifiables of which 1-3 wt. % are in form of triterpene esters and the remaining part in form of karitene and/or other typical constituents of the unsaponifiable fraction. The remaining 97-99 wt. % of the composition are glycerides in forms of mono-, di- or triglycerides.

The exact fatty acid composition for shea butter stearine varies as it is a natural raw material and grows in different parts of Africa.

A reaction with ethanol and shea butter with sodium ethylate as a catalyst would typically result in a composition between the following ranges:

|   | Min | Max |   |
|---|---|---|---|
| Ethyl oleate | 25 | 35 | wt. % |
| Ethyl stearate | 60 | 75 | wt. % |
| Ethyl palmitate | 2 | 8 | wt. % |
| Ethyl linoleate | 1 | 5 | wt. % |
| Unsaponifiable matter | 1 | 3 | wt. % |

All the described alternative embodiments above or parts of an embodiment can be freely combined without departing from the inventive idea as long as the combination is not contradictory.

All percentages and ratios are calculated by weight unless clearly indicated otherwise.

Other features and uses of the invention and their associated advantages will be evident to a person skilled in the art upon reading the description and the examples.

It is to be understood that this invention is not limited to the particular embodiments shown here. The embodiments are provided for illustrative purposes and are not intended to limit the scope of the invention since the scope of the present invention is limited only by the appended claims and equivalents thereof.

EXAMPLES

Example 1

Production of Shea Butter Oil Ethylate

The raw material used was:

Shea butter oil characterized by being liquid and with a triterpene ester content of 10 wt %.

Ethanol containing 99.5 wt % ethanol originating from sugar cane.

The catalyst was NaOEt (NaOCH2CH3).

Citric Acid:

5000 g of the shea butter oil, refined, bleached and deodorized according to standard procedure, was blended with ethanol (1250 g). 50 gram of the catalyst was added and the mixture blended and heated at 1 atm by vigorous stirring. When the temperature reached 75° C. the temperature was kept at 75° C. for 30 minutes in order for the reaction to reach steady state. After the 30 minutes reaction time the stirring was stopped to allow the glycerol to sediment at the bottom. After 30 minutes of separation two phases were seen. The upper phase (the ester phase) and a lower phase (glycerol phase) were seen. The glycerol phase was removed and weighed (435 g). Another 12.5 grams of catalyst were added to the remaining phase under stirring and the temperature increased to 75° C. and then kept at 75° C. for 30 minutes, 1 atm and vigorous stirring to once again reach steady state and a low mono glyceride content (below 1 wt %). The stirring was turned off to allow a glycerol phase to appear. The glycerol phase was once again removed (35 g). The ester was washed with water to stop reaction and remove traces of soap and then dried. The excess of ethanol was removed during the drying process. The theoretical yield would be 4675 gram, and 4200 grams were collected. The final product was characterized by comprising three classes of molecules; monoglycerides, fatty acid ethyl esters and triterpene (TTP) esters.

The mono glyceride content was less than 1 wt %, the TTP ester content was approximately 10 wt % and the ethyl ester content was approximately 89 wt %.

Three classes of triterpene esters were identified/detected; triterpene acetate, triterpene cinnamate and triterpene oleate (and other long chain fatty acids). About 3 wt. % triterpene acetates, about 5 wt. % of triterpene cinnamates and less than 2% of triterpene esters of long chain fatty acids. So most original triterpene cinnamates remain hut some reacts with the ethanol and creates ethyl cinnamate.

The ethyl long chain fatty acid content contained a number of esters.

| | |
|---|---|
| Ethyl oleate | 52.4% |
| Ethyl stearate | 24.3% |
| Ethyl palmitate | 5.2% |
| Ethyl linoleate | 6.2% |
| unsaponifiable | 9.7% |
| Other | 2.2% |
| Ethyl cinnamate | 2000 ppm |

The ethyl cinnamate level was determined to 2000 ppm.

Experiment 2: Bleaching

The standard procedure of bleaching. 3500 grams from experiment 1 was heated to 95° C. (10 mbar). The vacuum was released and 7 grams of bleaching earth was added (Tonsil). During the bleaching (20 minutes) the temperature was kept at 95° C., (10 mbar) and with stirring. The vacuum was released and then the product was filtered via a 5 micron filter.

| | |
|---|---|
| Ethyl oleate | 52.6% |
| Ethyl stearate | 24.4% |
| Ethyl palmitate | 5.2% |
| Ethyl linoleate | 6.3% |
| Unsaponifiable | 9.4% |
| Other | 2.1% |
| Ethyl cinnamate | 1600 Ppm |

The ethyl cinnamate was determined to 1600 ppm

Experiment 3: Deodorisation 100° C.

350 gram of the ester in experiment 1 was deodorized (100° C., 2 mbar, 20 g/h steam) for 30 minutes.

The remaining contained 9 wt. % of unsaponifiable in form of Triterpene esters. The ethyl ester content was 90%.

| | |
|---|---|
| Ethyl oleate | 52.5% |
| Ethyl stearate | 24.5% |
| Ethyl palmitate | 5.3% |
| Ethyl linoleate | 6.2% |
| unsaponifiable | 9.4% |
| Other | 2.1% |
| Ethyl cinnamate | 370 Ppm |
| Yield | 99% |

Experiment 4: Deodorisation 110° C.

350 gram of the ester in experiment 1 was deodorized (110° C. 2 mbar, 20 g/h steam) for 30 minutes.

The remaining contained 9 wt. % of unsaponifiable in form of Triterpene esters. The ethyl ester content was 90%.

| | |
|---|---|
| Ethyl cinnamate | 10 ppm |
| Yield | 99% |

Experiment 5: Deodorisation 120° C.

350 gram of the ester in experiment 1 was deodorized (120° C., 2 mbar, 20 g/h steam) for 30 minutes.

The remaining contained 9 wt. % of unsaponifiable in form of Triterpene esters. The ethyl ester content was 90%.

| | | |
|---|---|---|
| Ethyl cinnamate | 12 Ppm | |
| Yield | 98% | |

Experiment 6: Deodorisation 130° C.

350 gram of the ester in experiment 1 was deodorized (130° C., 2 mbar, 20 g/h steam) for 30 minutes.

The remaining contained 9 wt. % of unsaponifiable in form of Triterpene esters. The ethyl ester content was 90%.

| | |
|---|---|
| Ethyl cinnamate | <10 Ppm |
| yield | 96% |

Experiment 7: Deodorisation 140° C.

350 gram of the ester in experiment 1 was deodorized (140° C., 2 mbar, 20 g/h steam) for 30 minutes.

The remaining contained 10 wt. % of unsaponifiable in form of Triterpene esters. The ethyl ester content was 90%.

| | |
|---|---|
| Ethyl oleate | 52.1% |
| Ethyl stearate | 24.1% |
| Ethyl palmitate | 5.2% |
| Ethyl linoleate | 6.1% |
| unsaponifiable | 10.3% |
| Other | 2.1% |
| Ethyl cinnamate | <10 Ppm |
| Yield | 90% |

Experiment 8: Deodorisation 150° C.

350 gram of the ester in experiment 1 was deodorized (150° C., 2 mbar, 20 g/h steam) for 30 minutes.

The remaining contained 15 wt. % of unsaponifiable in form of Triterpene esters. The ethyl ester content was 84%.

| | |
|---|---|
| Ethyl oleate | 49.0% |
| Ethyl stearate | 22.6% |
| Ethyl paimitate | 4.9% |
| Ethyl linoleate | 6.0% |
| unsaponifiable | 15.6% |
| Other | 1.9% |
| Ethyl cinnamate | <10 Ppm |
| Yield | 55% |

Table 1

Summary of Yield from the deodorisation step.

| | Ethyl cinnamate | Yield |
|---|---|---|
| Experiment 1 | 2000 ppm | % |
| Experiment 2 | 1600 ppm | % |
| Experiment 3 | 370 ppm | 99 wt % |
| Experiment 4 | 10 ppm | 99 wt % |
| Experiment 5 | 12 ppm | 98 wt % |
| Experiment 6 | <10 ppm | 96 wt % |
| Experiment 7 | <10 ppm | 90 wt % |
| Experiment 8 | <10 ppm | 55 wt % |

Experiment 9

Bleaching: 6 Mt of Lipex SheaLight with an ethyl cinnamate level of 2200 ppm was added to a 10 M3 reactor. The product was 1 was heated to 95° C. (10 mbar), The vacuum was released and 120 kg of bleaching earth was added (Tonsil). During the bleaching (60 minutes) the temperature was kept at 95° C., (10 mbar) and with stirring, The vacuum was released and then the product was filtered via a 5 micron filter, to remove bleaching earth. The product were then recirculated into the reactor and underwent a steam deodorisation, 2 hours at 120° C., 1 mbar pressure. The level of Ethyl Cinnamate was 400 ppm. The yield for (including bleaching and steam deodorisation) was 97%.

Experiment 10 Evaluation of Odor Threshold Value

Nine persons were testing in a blind test five samples containing different levels (400, 600, 800, 1600 and 2000 ppm) of ethyl cinnamate.

The panelists were first allowed to smell 100 wt. % of ethyl cinnamate to learn which odor to identify. Then the panelist did receive 5 bottles containing different levels of ethyl cinnamate. The panelists were allowed to add sample on the skin to identify the odor.

Three panelists claimed to smell the ethyl cinnamate in all samples while one did not smell in any sample.

| PPM | persons claimed smell ethyl cinnamate | persons claimed they could not smell ethyl cinnamate |
|---|---|---|
| 400 | 0 | 9 |
| 600 | 3 | 6 |
| 800 | 6 | 3 |
| 1600 | 8 | 1 |
| 2000 | 8 | 1 |

The odour threshold for ethyl cinnamate in a matrix comprising long chain alkyl esters is thus estimated to be 700 ppm, defined as the level where 50% of the testers do not smell the test substance.

The invention claimed is:

1. An ingredient composition comprising:
    a) 81-97 wt % of at least one short chain alcohol alkyl ester, selected from the group consisting of ethyl alkyl ester, methyl alkyl ester, propyl alkyl ester, and isopropyl ester;
    b) 3-19 wt % of triterpene ester; and
    c) 1100 ppm or less of at least one short chain alcohol cinnamic ester.

2. The ingredient composition of claim 1, wherein the at least one short chain alcohol alkyl ester is at least partially from a natural source.

3. The ingredient composition of claim 1, wherein at least one of the triterpene esters is a cinnamic triterpene ester.

4. The ingredient composition of claim 1, wherein the at least one short chain alcohol cinnamic ester is ethyl cinnamate, methyl cinnamate, propyl cinnamate or isopropyl cinnamate.

5. The ingredient composition of claim 1, wherein the at least one short chain alcohol cinnamic ester is ethyl cinnamate.

6. The ingredient composition of claim 1, wherein the ingredient composition comprises 800 ppm or less of the at least one short chain alcohol cinnamic ester.

7. The ingredient composition of claim 1, wherein the ingredient composition comprises 700 ppm or less of the at least one short chain alcohol cinnamic ester.

8. The ingredient composition of claim 1, wherein the ingredient composition comprises 600 ppm or less of the at least one short chain alcohol cinnamic ester.

9. The ingredient composition of claim 1, wherein the ingredient composition comprises 400 ppm or less of the at least one short chain alcohol cinnamic ester.

10. The ingredient composition of claim 1, wherein the ingredient composition comprises 200 ppm or less of the at least one short chain alcohol cinnamic ester.

11. A personal care application comprising the ingredient composition of claim 1.

12. A cosmetic application comprising the ingredient composition of claim 1.

13. A skin care formulation comprising the ingredient composition of claim 1.

14. A hair color formulation comprising the ingredient composition of claim 1.

15. A lip care formulation comprising the ingredient composition of claim 1.

16. A colour cosmetic formulation comprising the ingredient composition of claim 1.

17. A sun care application comprising the ingredient composition of claim 1.

18. A lotion comprising the ingredient composition of claim 1.

19. An ointment comprising the ingredient composition of claim 1.

20. A cream comprising the ingredient composition of claim 1.

21. The ingredient composition of claim 1, wherein the ingredient composition functions as a constituent in soft-shelled capsules.

22. A food application comprising the ingredient composition of claim 1.

23. The ingredient composition of claim 1, wherein the ingredient composition functions as a release agent in a food application.

* * * * *

UNITED STATES PATENT AND TRADEMARK OFFICE
CERTIFICATE OF CORRECTION

PATENT NO. : 11,306,272 B2  
APPLICATION NO. : 16/093167  
DATED : April 19, 2022  
INVENTOR(S) : Jari Alander et al.

Page 1 of 1

It is certified that error appears in the above-identified patent and that said Letters Patent is hereby corrected as shown below:

In the Claims

Claim 1, Column 12, Line 60, "b) 3-19 wt % of triterpene ester; and" should read --b) 3-19 wt % of triterpene esters; and--.

Signed and Sealed this  
Twenty-first Day of June, 2022

Katherine Kelly Vidal  
*Director of the United States Patent and Trademark Office*